United States Patent [19]

Noveroske

[11] 4,062,962
[45] Dec. 13, 1977

[54] SUBSTITUTED PYRIDINES AS SYSTEMIC PLANT PROTECTANTS

[75] Inventor: Robert L. Noveroske, Midland, Mich.

[73] Assignee: The Dow Chemical Company, Midland, Mich.

[21] Appl. No.: 656,458

[22] Filed: Feb. 9, 1976

Related U.S. Application Data

[63] Continuation of Ser. No. 551,820, Feb. 21, 1975, abandoned, which is a continuation-in-part of Ser. No. 393,856, Sept. 4, 1973, abandoned, which is a continuation-in-part of Ser. No. 269,792, July 7, 1972, abandoned.

[51] Int. Cl.$^2$ .............................................. A01N 9/22
[52] U.S. Cl. .............................. 424/263; 424/DIG. 8
[58] Field of Search ........................ 424/263, DIG. 8

[56] References Cited

U.S. PATENT DOCUMENTS 3,244,722  4/1966  Johnston et al. ...................... 71/94
3,705,170  12/1972  Torba .................................... 424/263
3,711,486  1/1973  Torba .................................... 424/263

Primary Examiner—V. D. Turner
Attorney, Agent, or Firm—S. Preston Jones; C. Kenneth Bjork

[57] ABSTRACT

A method for protecting plants for extended time periods from attack by soil-borne plant disease organisms, which method comprises applying to plant parts, a nonphytotoxic but plant protecting amount of a systemic plant protectant corresponding to the formula

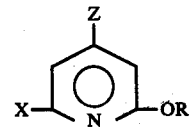

wherein X represents chloro, fluoro or bromo; Z represents trichloromethyl, dichloromethyl or dichlorofluoromethyl and R represents lower alkyl of 1 to 4 carbon atoms or phenyl.

15 Claims, No Drawings

SUBSTITUTED PYRIDINES AS SYSTEMIC PLANT PROTECTANTS

CROSS-REFERENCE TO RELATED APPLICATIONS

This is a continuation of application Ser. No. 551,820, filed Feb. 21, 1975, now abandoned which is a continuation-in-part of application Ser. No. 393,856, filed Sept. 4, 1973, now abandoned which is a continuation-in-part of application Ser. No. 269,792, filed July 7, 1972, now abandoned.

BACKGROUND OF THE INVENTION

This invention relates to a method for protecting plants from attack for extended time periods by soil-borne plant disease organisms which comprises contacting seeds or plant parts with a systemic plant protectant corresponding to the formula

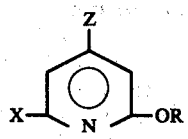

wherein X represents chloro, fluoro or bromo; Z represents trichloromethyl, dichloromethyl or dichlorofluoromethyl and R represents lower alkyl of 1 to 4 carbon atoms or phenyl.

In U.S. Pat. No. 3,244,722, issued Apr. 5, 1966, there are described and claimed, among other related compounds, those corresponding to the formula:

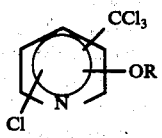

wherein R is alkyl of 1 to 18 carbon atoms.

Exemplary compounds listed in this patent include 2-chloro-4-methoxy-6-(trichloromethyl)pyridine, 2-chloro-6-methoxy-4-(trichloromethyl)pyridine, 5-chloro-2-methoxy-4-(trichloromethyl)pyridine and 3-chloro-2-methoxy-4-(trichloromethyl)pyridine. As reported in this patent, various compounds disclosed therein are useful as herbicides; various other compounds are useful in the control of pest fish and aquatic insects; and other compounds are taught to be useful as insecticides and anthelmintic agents for warm-blooded animals.

It has now been found that within the broad genus of pyridine compounds taught in U.S. Pat. No. 3,244,722, the specific compounds having a chlorine, fluorine or bromine atom in the 6-ring position, a dichloromethyl, trichloromethyl or dichlorofluoromethyl group in the Y-ring position and an alkoxy or phenoxy group in the 2-ring position surprisingly and unexpectedly exhibit superior and unique properties in being able to systemically protect plants for extended periods of time from attack by soil-borne plant diseases. This kind of activity is not exhibited by isomers or analogs of compounds employed in the herein disclosed method. The outstanding activity of these specific compounds is particularly unexpected since these compounds are generally not effective at the same application rates against the same organisms outside of the plant itself, i.e., when the compounds are used as a pre-plant soil sterilant or fumigant.

It is an object of the present invention to provide an improved method for systemically protecting plants from attack, for extended periods of time, by soil-borne plant disease organisms.

It is a further object of the present invention to provide a method whereby long-lived activity in plants against soil-borne plant disease organisms is achieved, with toxicants which are generally not effective in controlling these same organisms outside of the plants.

One of the advantages of the present method is that by the mode of action of the active toxicant, plant diseases can be eliminated from infected plants and non-infected plants can be protected from attack.

The present method also offers a practical advantage in that there is no need to employ the additional time and labor required by conventional preplant sterilization with soil fumigants.

A further practical advantage of the present method is that the active compounds are used in amounts which are the equivalent of ounces to several pounds of the active ingredient on a per acre basis as against the conventional soil fertilization practices which require many pounds and hundreds of pounds of active material per acre.

SUMMARY OF THE INVENTION

The present invention is directed to a method for systemically protecting plants for extended time periods from attack by soil-borne disease organisms.

According to the present invention it has been discovered that soil-borne plant disease organisms which attack plants may be controlled for extended periods of time by contacting plant parts with a substantially non-phytotoxic but plant-protecting amount of a systemic plant protectant corresponding to the formula:

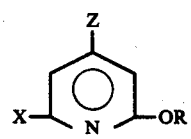

In this and succeeding formulae, X represents chloro, fluoro or bromo; Z represents trichloromethyl, dichloromethyl or dichlorofluoromethyl and R represents lower alkyl of 1 to 4 carbon atoms or phenyl.

In the present specification and claims, the term "alkyl" is employed to designate straight or branched chain alkyl groups containing from 1 to 4 carbon atoms, such as, for example, methyl, ethyl, normal propyl, isopropyl, normal butyl, secondary butyl and tertiary butyl.

In the present specification and claims, the term "plant part" is employed to designate all parts of a plant and includes seeds, bulbs, stolons, tubers, rhizomes, ratoons, corms, the root system, hereinafter commonly referred to as root, the crown, stalk, stem, foliage or leaf system, fruit or flower.

In the present specification and claims, the term "extended time" designates a minimum time period of 3 weeks during which plants or plant parts contacted with a minimum amount of the active compounds of the present invention are protected from attack by soil-borne plant disease organisms.

In the present specification and claims, the term "systemic" defines the translocation of the active compound employed in the present method through the plant whereby they selectively accumulate principally in the underground portions of the plant. The following illustrative example will further the understanding of the term systemic as used herein. If the active compounds are applied to seeds, accumulation of the active compound is found mainly in the underground system of the germinating seed; if applied to storage organs (bulbs, stolons, tubers, rhizomes, ratoons or corms), the active compound will absorb into the plant tissue and upon active growth following dormancy, the compound will be found mainly in the below-ground portion of the growing plant; if applied to the above-ground portions of the plant, the active compounds downwardly translocate and principally accumulate in the underground system; and application of the active compound adjacent the underground portions of the plant gives remarkably fast protection by the compound, due to the proximity of the point of application to the area of chemical accumulation, and to the fact there is mainly no translocation away from the underground system.

Examples of compounds which are active agents in the present method include:

6-Chloro-(fluoro- or bromo-)-2-methoxy-4-(trichloromethyl)pyridine;
6-Chloro-(fluoro- or bromo-)-2-ethoxy-4-(trichloromethyl)pyridine;
6-Chloro-(fluoro- or bromo-)-2-propoxy-4-(trichloromethyl)pyridine;
6-Chloro-(fluoro- or bromo-)-2-isopropoxy-4-(trichloromethyl)pyridine;
6-Chloro-(fluoro- or bromo-)-2-n-butoxy-4-(trichloromethyl)pyridine;
6-Chloro-(fluoro- or bromo-)-2-sec.-butoxy-4-(trichloromethyl)pyridine;
6-Chloro-(fluoro- or bromo-)-2-phenoxy-4-(trichloromethyl)pyridine;
6-Chloro-(fluoro- or bromo-)-2-methoxy-4-(dichloromethyl)pyridine;
6-Chloro-(fluoro- or bromo-)-2-ethoxy-4-(dichloromethyl)pyridine;
6-Chloro-(fluoro- or bromo-)-2-propoxy-4-(dichloromethyl)pyridine;
6-Chloro-(fluoro- or bromo-)-2-isopropoxy-4-(dichloromethyl)pyridine;
6-Chloro-(fluoro- or bromo-)-2-n-butoxy-4-(dichloromethyl)pyridine;
6-Chloro-(fluoro- or bromo-)-2-sec.-butoxy-4-(dichloromethyl)pyridine;
6-Chloro-(fluoro- or bromo-)-2-tert.-butoxy-4-(dichloromethyl)pyridine;
6-Chloro-(fluoro- or bromo-)-2-phenoxy-4-(dichloromethyl)pyridine;
6-Chloro-(fluoro- or bromo-)-2-methoxy-4-(dichlorofluoromethyl)pyridine;
6-Chloro-(fluoro- or bromo-)-2-ethoxy-4-(dichlorofluoromethyl)pyridine;
6-Chloro-(fluoro- or bromo-)-2-propoxy-4-(dichlorofluoromethyl)pyridine;
6-Chloro-(fluoro- or bromo-)-2-isopropoxy-4-(dichlorofluoromethyl)pyridine;
6-Chloro-(fluoro- or bromo-)-2-n-butoxy-4-(dichlorofluoromethyl)pyridine;
6-Chloro-(fluoro- or bromo-)-2-sec.-butoxy-4-(dichlorofluoromethyl)pyridine;
6-Chloro-(fluoro- or bromo-)-2-tert.-butoxy-4-(dichlorofluoromethyl)pyridine;
6-Chloro-(fluoro- or bromo-)-2-phenoxy-4-(dichlorofluoromethyl)pyridine;

Compositions containing one or more of the active compounds of the present invention have been found to be very effective in the control of plant diseases caused by soil-borne plant disease organisms either before or after the plant has been attacked by said disease organisms.

Representative soil-borne plant disease organisms which attack the below ground portion of plants, and which are controlled by the present method include soil disease fungi such as Verticillium, Rhizoctonia, Phytophthora and Pythium and gram-negative bacteria such as Pseudomonas.

Control of soil-borne plant disease by the present invention is achieved, for example, in cereal crops such as corn, wheat, barley, rye, oats, rice and sorghum; vegetable crops such as tomatoes, peppers, lettuce, onions, cabbage, broccoli, squash, cucumbers, cauliflower, etc., legumes such as peanuts, soybeans, peas and alfalfa; root crops such as turnips, beets, carrots, white potatoes, sweet potatoes and yams; fiber crops such as cotton, flax and hemp; fruit crops such as apples, bananas, cantaloupes, cherries, dates, figs, grapes, pineapples, grapefruit, lemons, limes, oranges, peaches, pears, plums, strawberries and watermelon; oil crops such as castorbean, copra, olives, palms, rubber and sunflower; stimulants such as cocoa, coffee, tea and tobacco; sugar crops such as sugar cane and sugar beets; turf including bent grass and blue grass, rye and fescue; ornamentals such as chrysanthemums, zinnias, carnations, lilies, violets, petunias, marigolds, philodendrons, schefflera, dracaena, wax plants, jade plant, ivy, ferns, rubber plants, cactus and dieffenbachia; woody ornamentals such as pines, roses, rhododendron, azaleas, boxwood, spruce and the like. While the above lists a variety of crop plants which may be treated by the practice of the present invention, it is to be understood that the present method is not restricted to the above list of crop plants.

Generally in the actual practice of the method of the present invention, a plant protecting amount of the active toxicant compounds can be applied to the plant or plant part by a variety of convenient procedures. Such procedures include soil incorporation whereby compositions containing the active toxicant are mechanically mixed with the soil; applied to the surface of the soil and thereafter dragged, disced or rototilled into the soil; or transported into the soil with a liquid carrier such as by injection, spraying or irrigation. Additionally, a plant protecting amount of the active toxicant compounds can be employed in sprays, gels or coatings for above-ground applications or drenched onto the soil surface. In additional application methods, the active toxicant can be applied by vapor transfer; added in liquid or solid composition to hydroponic operations; seed treatment operations and by conventional plant part coating operations or other techniques known to those skilled in the art. The only limitation upon the mode of application employed is that it must be one which will allow the toxicant to come in contact with plants or plant parts.

The exact dosage of the active toxicant employed can be varied depending upon the specific plant, its stage of development, hardiness, the mode of application and its growth media. Generally, the active ingredient should be present in an amount equivalent to from about 50 micrograms to about 140 grams or more per plant on a per plant basis. Translating this into conventional application rates, this amount is equivalent to from about 0.0005 pound to about 10 pounds or more of the active ingredient on a per acre basis, as chemical available to the plant.

It will be appreciated that on a per plant basis, seed treatment of small seeded plant species such as grasses, carrots, and the like will actually require much smaller amounts than 50 micrograms per plant. Generally, rates in the range of 1/32 to about 8 ounces per 100 pounds of seeds will be optimum for seed treatment among the diversity of plant species. For practices such as conventional tobacco transplant treatment or in-furrow soil treatment of plants such as soybeans at seeding and the like, an amount of active toxicant approximately equal to 8 to about 32 milligrams would be utilized on a per plant basis.

Larger amounts of the active ingredient may advantageously be applied when treatments are employed which distribute the material throughout the soil. For example, when the active ingredient is applied as an atplant row treatment or as an early or mid-season postplant side dress treatment, those amounts of chemical not proximal to plant roots are essentially unavailable to the plant and therefore not effective as set forth hereinabove. In such practices, the amount of the active ingredient employed needs to be increased to rates as high as about 20 pounds per acre or higher to assure that the requisite effective quantity of active ingredient is made available to the plants.

The present invention can be carried out by employing the pyridine compounds directly, either singly or in combination. However, the present invention also embraces the employment of liquids, dusts, waxes, gels, jellies, wettable powders, granules or encapsulated compositions containing at least one of said compounds as active ingredient. In such usage, the compound or compounds can be modified with one or more of a plurality of additaments or soil-modifying adjuvants including fertilizers, nematicides, herbicides, insecticides or other pesticidal adjuvants or inert solvents, inert liquid carriers and/or surface active dispersing agents and coarsely or finely divided inert solids. The augmented compositions are also adapted to be employed as concentrates and subsequentially diluted with additional inert carrier to produce other compositions in the form of dusts, sprays, granules, washes or drenches. In compositions where the adjuvant is a coarsely or finely divided solid, a surface active agent or the combination of a surface active agent and a liquid additament, the adjuvant cooperates with the active component so as to facilitate the invention. Whether the composition is employed in liquid, wettable powder, gel, wax, jelly, dust, granule or encapsulated form, the active compound will normally be present in an amount of from about 2 to 98 percent by weight of the total composition.

In the preparation of dust, wettable powders or other solid compositions, the toxicant products can be compounded with any of the finely divided solids, such as pyrophyllite, talc, chalk, gypsum, fuller's earth, bentonite, attapulgite, modified clays, starch, casein, gluten and the like. In such operations, the finely divided carrier is ground or mixed with the toxicant or wet with a solution of the toxicant in a volatile organic solvent. Also, such compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided attapulgite, bentonite, diatomite, or the like.

Additionally, gels containing the desired amount of one of the active compounds can be prepared by dispersing the active compound in an inert aqueous or organic based liquid and thereafter treating said mixture with a gelling medium such as crosslinked alkaline salts of polyacrylic acid, methyl cellulose, carboxymethyl cellulose, tertiary butyl styrene, modified clays or other conventional gelling mediums.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of inert water-immiscible solvent, emulsifying agent and water. Preferred dispersing agents which can be employed in these compositions, are oil-soluble materials including non-ionic emulsifiers such as the condensation products of alkylene oxides with the inorganic acids, polyoxyethylene derivatives or sorbitan esters, complex ether alcohols and the like. Also, oil-soluble ionic emulsifying agents such as mahogany soaps can be used. Suitable inert organic liquids which can be employed in the compositions include vegetable oils or petroleum oils and distillates, toluene, liquid halohydrocarbons and synthetic organic oils. The surface-active dispersing agents are usually employed in liquid compositions and in the amount of from 0.1 to 20 percent by weight of the combined weight of the dispersing agent and active compound.

In addition, other compositions containing the desired amount of effective agent can be prepared by dispersing the toxicant in an inert organic liquid such as acetone, methylene chloride, chlorobenzene and petroleum distillates. The preferred inert organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400° F. at atmospheric pressure and having a flash point above 80° C. The proportion of the compounds of this invention employed in a suitable solvent may vary from about 2 to about 50 percent or higher. Additionally, the active components can be compounded with waxes or petroleum jellies to prepare viscous or semi-solid treating compositions.

A preferred liquid composition includes the use of the active compound or compounds in combination with surface active dispersant agents only. In such compositions, it is preferred to use ionic and non-ionic blends of such dispersant agents in combination with one or more of the active materials. A particular advantage of such a formulation is that phytotoxicity associated with certain inert solvents, such as, xylene, methylene chloride, and like materials can be avoided. Generally, the use of such formulations will results in compositions containing 75 percent or more of the active component.

Owing to the excellent suspensibility of the above formulation in water, it is convenient and often preferred to prepare and use aqueous concentrates as stock solutions themselves. In such practices, minor agitation results in a practical, stable formulation very adaptable for use in its concentrate form to treat soil in sprays or drenches. Additionally, if desired, the concentrates can be easily diluted with additional water for use as foliar spray treatments, soil drench streatments and the like.

Water miscible organic solvents such as lower alcohols or propylene glycol can be added to depress the freezing point and further cooperate with the above system in that they are essentially non-phytotoxic.

The expression "soil" is employed herein in its broadest sense to be inclusive of all conventional soils, as defined in Webster's New International Dictionary, Second Edition, Unabridged, published in 1937, G. C. Merriam Co., Springfield, Mass. Thus the term refers to any substance or medium in which plants may take root and grow, and is intended to include not only earth, but also compost, manure, muck, sand, synthetic growth mediums such as vermiculite and pearlite and the like, adapted to support plant growth.

DESCRIPTION OF THE PREFERRED EMBODIMENTS

In order that the present invention may be more fully understood, the following examples are given to illustrate the manner by which it can be practiced but, as such, should not be construed as limitations upon the overall scope of the same.

EXAMPLE I

A study was conducted following the practice of the present invention to determine the therapeutic effectiveness on tabacco plants of various systemic plant protectants disclosed herein.

Soil infected with the tabacco black shank pathogen *Phytophthora parasitica* var. *nicotianae* was uniformly mixed and placed in a predetermined number of 2-inch pots. To said pots were transplanted three to four week old tobacco seedlings of the "402" variety which had been grown in a disease free medium. At indicated intervals, sets of plants were drenched with dilutions of the test chemicals at hereinafter set forth dosages. Appropriate no-treatment checks were drenches with water only. Additionally, a transplant check treatment was utilized in the following manner:

At each time period mentioned above, plants growing in infected soil were removed, their roots washed free of contaminant soil, and transplanted into disease free soil. The time disease symptoms began to show in transplant checks established that time at which the disease organism was already established within the root system of the infected plants. Thus, any chemical control after that said time period can be taken as a measure of therapeutic effectiveness.

Test dispersions of each of the compounds 6-chloro-2-methoxy-4-(trichloromethyl)pyridine and 6-bromo-2-methoxy-4-(trichloromethyl)pyridine were prepared by dispersing the chemicals in acetone and thereafter diluting the solution with predetermined amounts of water to prepare dispersions containing 2.5, 10 and 40 parts of the test chemicals per million parts of the ultimate dispersion. Thereafter, the various test chemical dispersions were employed to treat separate groups of pots containing the seedlings as outlined above, by drenching 35 cubic centimeters of each of the dispersions onto the soil. After treatment, the plants were maintained under conditions conducive for good plant growth. Three weeks after treatment, the plants were examined for disease control. The results of this examination are set forth below in Table I.

TABLE I

| Test Compound Applied | Concentration of Test Chemical Applied to Soil in Part per Million by Weight of Ultimate Dispersion* | Percent Control of Phytophthora parasitica Days Tobacco Transplants Incubated in Soil before Test Chemical Added | | | |
|---|---|---|---|---|---|
| | | 0 | 1 | 2 | 3 |
| 6-Chloro-2-methoxy-4-(trichloromethyl)-pyridine | 40 | 100 | 100 | 100 | 60 |
| | 10 | 100 | 80 | 100 | 100 |
| | 2.5 | 100 | 0 | 0 | 0 |
| 6-Bromo-2-methoxy-4-(trichloromethyl)-pyridine | 40 | 100 | 100 | 100 | 100 |
| | 10 | 100 | 100 | 100 | 100 |
| | 2.5 | 80 | 20 | 80 | 40 |
| Transplant check | — | 100 | 100 | 20 | 0 |
| Solvent check | — | 0 | 0 | 0 | 0 |
| No-treatment check | — | 0 | 0 | 0 | 0 |

*dosage equivalent to 0.02, 0.005 and 0.0013 pounds of active material (test chemical) per acre assuming a normal planting rate of 6,000 plants per acre.

EXAMPLE II

A study was conducted to determine the effectiveness of the downward systemic translocation of the compounds on tobacco plants.

Five week old tobacco seedlings of the 402 variety were transplanted into 4-inch pots containing sandy loam soil of good nutrient value and which were uniformly infected with *Phytophthora parasitica* var. *nicotianae*. About ¾ of pot space at the top of the pot was left unfilled with soil and to each pot was added 100 milliliters of water. Thereafter a dry vermiculite soil cap was added to fill the pots and prevent chemical run-off into the soil. Each plant is thereafter sprayed with 2 milliliters of a test composition containing 6-chloro-2-methoxy-4-(trichloromethyl)pyridine as the sole active ingredient. Separate compositions were employed containing 2400, 1200, 600 and 150 parts by weight of the active toxicant per million parts of the ultimate compositions. After treatment, the plants were allowed to dry, the vermiculite caps removed and the plants were maintained under conditions conducive to good plant growth. Additional plants were left untreated to serve as control. Five days after treatment, both the treated and untreated plants were examined to determine the amount of disease control present. The results of this examination are set forth below in Table II.

TABLE II

| Active Compound Employed | Percent Control of Phytophthora parasitica at the Indicated Dosages of Active Compound in Part Per Million by Weight* | | | |
|---|---|---|---|---|
| | 2400 | 1200 | 600 | 150 |
| 6-Chloro-2-methoxy-4-(trichloro- | 100 | 100 | 50 | 25 |

TABLE II-continued

| Active Compound Employed | Percent Control of Phytophthora parasitica at the Indicated Dosages of Active Compound in Part Per Million by Weight* | | | |
|---|---|---|---|---|
| | 2400 | 1200 | 600 | 150 |
| methyl)pyridine | | | | |
| Control (untreated plants) | 0 | 0 | 0 | 0 |

*dosage rate equivalent to 2, 1, ½ and ¼ pounds of active compound per acre assuming an application rate of 100 gallons per acre.

EXAMPLE III

Soil infected with the tobacco black shank pathogen *Phytophthora parasitica* var. *nicotianae* was uniformly mixed and placed in 2-inch pots. To said pots were transplanted four week old tabacco seedlings of the 402 variety which had been grown in pathogen free soil. Test dispersions of each of the compounds 6-chloro-2-methoxy-4-(trichloromethyl)pyridine, 6-chloro-2-methoxy-4-(dichloromethyl)pyridine, and 6-chloro-2-methoxy-4-(dichlorofluoromethyl)pyridine were prepared by dispersing the chemicals in acetone and thereafter diluting the solution with water to prepare dispersions containing 100 and 25 parts by weight of each of the compounds per million parts of the ultimate dispersion. Thereafter, the various test dispersions were employed to treat separate pots containing the seedlings by pouring 40 cubic centimeters of each of the dispersions onto the soil, assuring root contact with sufficient chemical. Additional pots were treated with an aqueous acetone solution and water to serve as controls. After treatments, the plants were maintained under conditions conducive for good plant growth. Three and five weeks after treatment, the plants were examined for disease control. The results of this examination are set forth below in Table III.

TABLE III

| Active Compound Employed | Application Rate in ppm* | Percent Control of Phytophthora parasitica in Tobacco Seedlings | |
|---|---|---|---|
| | | 3 weeks | 5 weeks |
| 6-Chloro-2-methoxy-4-(trichloromethyl)-pyridine | 100 | 100 | 100 |
| | 25 | 100 | 50 |
| 6-Chloro-2-methyoxy-4-(dichloromethyl)-pyridine | 100 | 100 | 100 |
| | 25 | 0 | 0 |
| 6-Chloro-2-methoxy-4-(dichlorofluoromethyl)-pyridine | 100 | 100 | 100 |
| | 25 | 50 | 0 |
| Acetone Control | — | 0 | 0 |
| Water Control | — | 0 | 0 |

*equivalent to a dosage rate of 0.05 and 0.13 pounds of active compound per acre assuming an average planting rate of 6,000 plants per acre.

EXAMPLE IV

Soil infected with tobacco black shank pathogen *Phytophthora parasitica* var. *nicotianae* was uniformly mixed and placed in 6-inch pots. To said pots were transplanted four week old tobacco seedlings of the 402 variety which had been grown in pathogen free soil. Test dispersions of 6-fluoro-2-methoxy-4-(trichloromethyl)pyridine were prepared by dispersing the chemical in acetone and thereafter diluting the solution with water to prepare dispersions containing 150 and 37 parts by weight of the compound per million parts of the ultimate dispersion. Thereafter, the test dispersions were employed to treat separate pots containing the seedling by pouring 100 cubic centimeters of each of the dispersions onto the soil, assuring root contact with sufficient chemical. Additional pots were treated with an aqueous acetone solution and water to serve as controls. After treatments, the plants were maintained under conditions conducive for good plant growth. Three and five weeks after treatment, the plants were examined for disease control. The results of this examination are set forth below in Table IV.

TABLE IV

| Active Compound Employed | Application Rate in ppm* | Percent Control of Phytophthora parasitica in Tobacco Seedlings | |
|---|---|---|---|
| | | 3 Weeks | 5 Weeks |
| 6-Fluoro-2-methoxy-4-(trichloromethyl)pyridine | 150 | 100 | 100 |
| " | 37 | 100 | 100 |
| Acetone Control | — | 0 | 0 |
| Water Control | — | 0 | 0 |

*equivalent to dosage rate of 0.2 and 0.05 pounds of active compound per acre assuming a planting rate of 6,000 plants per acre.

EXAMPLE V

Soil infected with the tobacco black shank pathogen *Phytophthora parasitica* var. *nicotianae* was uniformly mixed and placed in 4-inch pots. To said pots were transplanted four week old tobacco seedlings of the 402 variety which had been grown in pathogen free soil. Test dispersions of 6-chloro-2-ethoxy-4-(trichloromethyl)pyridine, were prepared by dispersing the chemical in acetone and thereafter diluting the solution with water to prepare dispersions containing 100, 25, 6.2 and 1.5 parts by weight of the compound per million parts of the ultimate dispersion. Thereafter, the various test dispersions were employed to treat separate pots containing the seedling by pouring 70 cubic centimeters of each of the dispersions onto the soil assuring root contact with sufficient chemical. Additional pots were treated with an aqueous acetone solution and water to serve as controls. After treatments, the plants were maintained under conditions conducive for good plant growth. Three weeks after treatment, the plants were examined for disease control. The results of this examination are set forth below in Table V.

TABLE V

| Active Compound Employed | Application Rate in ppm* | Percent Control of Phytophthora Parasitica in Tobacco Seedlings 3 weeks |
|---|---|---|
| 6-Chloro-2-ethoxy-4-(trichloromethyl)-pyridine | 100 | 100 |
| " | 25 | 80 |
| " | 6.2 | 60 |
| " | 1.5 | 40 |
| Acetone | | |

TABLE V-continued

| Active Compound Employed | Application Rate in ppm* | Percent Control of Phytophthora Parasitica in Tobacco Seedlings 3 weeks |
|---|---|---|
| Control Water | — | 0 |
| Control | — | 0 |

*equivalent to a dosage rate of 0.09, 0.023, 0.006 and 0.0015 pound of active compound per acre assuming a planting rate of 6,000 plants per acre.

EXAMPLE VI

Soil infected with tobacco black shank pathogen *Phytophthora parasitica* var. *nicotianae* was uniformly mixed and placed in 2-inch pots. To said pots were transplanted four week old tobacco seedlings of the 402 variety which had been grown in pathogen free soil. Test dispersions of 6-chloro-2-butoxy-4-(trichloromethyl)pyridine were prepared by dispersing the chemical in acetone and thereafter diluting the solution with water to prepare dispersions containing 100, 25 and 6.2 parts by weight of the compound per million parts of the ultimate dispersion. Thereafter, the various test dispersions were employed to treat separate pots containing the seedling by pouring 35 cubic centimeters of each of the dispersions onto the soil, assuring root contact with sufficient chemical. Additional pots were treated with an aqueous acetone solution and water to serve as controls. After treatments, the plants were maintained under conditions conducive for good plant growth. Four days and three weeks after treatment, the plants were examined for disease control. The results of this examination are set forth below in Table VI.

TABLE VI

| Active Compound Employed | Application Rate in ppm* | Percent Control of Phytophthora parasitica in Tobacco Seedlings 4 Days | 3 Weeks |
|---|---|---|---|
| 6-Chloro-2-butoxy-4-(trichloromethyl)-pyridine | 100 | 100 | 100 |
| " | 25 | 100 | 100 |
| " | 6.2 | 100 | 50 |
| Acetone Control | — | 0 | 0 |
| Water Control | — | 0 | 0 |

*equivalent to a dosage rate of 0.046, 0.0115 and 0.003 pounds of the active compound per acre assuming a planting rate of 6,000 plants per acre.

EXAMPLE VII

Soil infected with tobacco black shank pathogen *Phytophthora parasitica* var. *nicotianae* was uniformly mixed and placed in 2-inch pots. To said pots were transplanted four week old tobacco seedlings of the 402 variety which had been grown in pathogen free soil. Test dispersions of the compound 6-chloro-2-phenoxy-4-(trichloromethyl)pyridine was prepared by dispersing the chemical in acetone and thereafter diluting the solution with water to prepare dispersions containing 100 and 25 parts by weight of the compound per million parts of the ultimate dispersion. Thereafter, the test dispersion was employed to treat pots containing the seedlings by pouring 40 cubic centimeters of the dispersion onto the soil, assuring root contact with sufficient chemical. Additional pots were treated with an aqueous acetone solution and water to serve as controls. After treatment, the plants were maintained under conditions conducive for good plant growth. Eleven days after treatment, the plants were examined for disease control. The results of this examination are set forth below in Table VII.

TABLE VII

| Active Compound Employed | Application Rate in ppm* | Percent Control of Phytophthora parasitica in Tobacco Seedlings 11 Days |
|---|---|---|
| 6-Chloro-2-phenoxy-4-(trichloromethyl)-pyridine | 100 | 100 |
| | 25 | 100 |
| Acetone Control | — | 0 |
| Water Control | — | 0 |

*equivalent to a dosage rate of 0.05 and 0.013 pounds of active compound per acre assuming an average planting rate of 6,000 plants per acre.

EXAMPLE VIII

An acetone concentrate was prepared by admixing 71 milligrams of 6-chloro-2-methoxy-4-(trichloromethyl)-pyridine with 2 milliliters of acetone. Four two-fold serial dilutions were prepared from this concentrate by diluting portions of the concentrate with predetermined amounts of acetone. One-half milliliter aliquots of each dilution were applied equally to 1-ounce seedlots of Little Marvel pea seeds. This application procedure resulted in an equivalent to treating 100 pounds of seeds at a dilution rate of 1, ½, ¼, ⅛, and 1/16 ounce of active compound. Twenty-five seeds from each treatment were thereafter planted in pots of soil containing *Pythium ultimum*. Additional seeds, 25 treated with acetone alone and 25 untreated were also planted to serve as controls. After planting, the pots containing the seeds were watered and placed in a biochamber at 65° C. for 5 days. The pots were removed and placed in a greenhouse under conditions conducive to good plant growth for 1 week. The pots were thereafter examined to determine the number of seeds from each treatment and the top growth weight of the plants. After this test, an additional test was run in a manner identical to the above. The results of these examinations are set forth in Table VIII.

TABLE VIII

| | | Test 1 | | | Test 2 | | |
|---|---|---|---|---|---|---|---|
| Compound Employed | Dosage of Active Compound Per 100 Pounds of Seed in Ounces | Number of Seeds Which Emerge of 25 Seeds Planted | Percentage of Seeds Which Emerge of 25 Seeds Planted | Average Plant Weight in Grams | Number of Seeds Which Emerge of 25 Seeds Planted | Percentage of Seeds Which Emerge of 25 Seeds Planted | Average Plant Weight in Grams |
| 6-Chloro-2-methoxy-4-(tri-chloro- | 1 | 24 | 96 | 5.5 | 23 | 92 | 5.3 |
| | 1/2 | 22 | 88 | 4.9 | 22 | 88 | 5.0 |
| | 1/4 | 22 | 88 | 4.6 | 17 | 68 | 3.5 |
| | 1/8 | 21 | 84 | 3.1 | 14 | 56 | 3.9 |

TABLE VIII-continued

| | | Test 1 | | | Test 2 | | |
|---|---|---|---|---|---|---|---|
| Compound Employed | Dosage of Active Compound Per 100 Pounds of Seed in Ounces | Number of Seeds Which Emerge of 25 Seeds Planted | Percentage of Seeds Which Emerge of 25 Seeds Planted | Average Plant Weight in Grams | Number of Seeds Which Emerge of 25 Seeds Planted | Percentage of Seeds Which Emerge of 25 Seeds Planted | Average Plant Weight in Grams |
| methyl)-pyridine | 1/16 | 19 | 76 | 3.4 | 18 | 72 | 3.2 |
| Acetone Control | — | 8 | 32 | 2.5 | 8 | 32 | 1.9 |
| No Treatment Control | — | 11 | 42 | 2.6 | 10 | 40 | 2.3 |

EXAMPLE IX

6-Chloro-2-methoxy-4-(trichloromethyl)pyridine was diluted with water to prepare aqueous dispersions having predetermined contents of the active compound. These dispersions were sprayed onto field plots of sandy loam soil in which cotton seeds had been planted. Each plot was approximately 192 square feet. The soil had a high content of the causative organism of root rot and seeding damping off, i.e., Rhizoctonia sp. The seed rows in each separate plot were sprayed, with one of the aqueous dispersions to give plots which had been treated with an equivalent of 1, 2, 4 and 8 ounces of the active agent per acre. Separate plots were left untreated to serve as a control. Counts were made of the number of plants growing 21 days after planting and 30 days after planting. At the end of a 7-month growth period, seeds were harvested from the plants and weighed. The results of this study are set forth below in Table IX.

TABLE IX

| Test Compound | Dosage Rate in Ounces of Active Agent/Acre | Average Plant Counts 21 Days | 30 Days | Seed Yield in Pounds | Seed Yield as Percent of Control |
|---|---|---|---|---|---|
| 6-Chloro-2-methoxy-4-(trichloro methyl)pyridine | 8 | 170 | 206 | 2.8 | 97 |
| | 4 | 224 | 216 | 3.3 | 114 |
| | 2 | 232 | 231 | 3.7 | 128 |
| | 1 | 217 | 212 | 3.3 | 114 |
| Untreated Control | — | 120 | 107 | 2.9 | 100 |

EXAMPLE X

Soil infected with the vascular wilt organism *Verticillium albo-atrum* was uniformly mixed and used to fill 6-inch pots to within 3 ½ inches from the top. The pots were treated with aqueous dispersions of 6-chloro-2-methoxy-4-(trichloromethyl)pyridine containing predetermined amounts of the compound. This treatment gave pots which had been treated with the equivalent of 0.5, 1 and 2 pounds of the compound per acre. Additional infected soil was added to the pots to within 1 ½ inch of the top. Five cotton seeds were planted in each pot and the pots were watered lightly. Sterile soil was added to the pots to cover the seeds. Additional pots were also prepared as above except they were not treated with chemical to serve as controls. The pots were thereafter maintained under conditions conducive to good plant growth. Eight weeks after treatment, the pots were examined to determine the percent of disease control. The results of this study are set forth below in Table X.

TABLE X

| Test Compound | Dosage in Pounds per Acre | Percent *Verticillium* Disease Symptoms |
|---|---|---|
| 6-Chloro-2-methoxy-4-(trichloro-methyl)pyridine | 2 | 2.8 |
| | 1 | 5.6 |
| | 0.5 | 5.6 |
| Untreated Control | — | 35 |

EXAMPLE XI

An aqueous dispersion was prepared by diluting a predetermined amount of 6-chloro-2-methoxy-4-(trichloromethyl)pyridine in a predetermined amount of water. The dispersion was employed as a tobacco transplant water treatment and the dilution rate was predetermined so as to deliver the transplant water at a treatment rate of 8 ounces (0.5 pounds) of the active toxicant per acre. The dispersion was applied to field plots at the time of setting tobacco transplants (N.C.-2326 variety) which had also been treated with O-ethyl S,S-dipropyl-phosphorodithioate, a nematicide. Additional plots containing tobacco plants which were treated with the nematicide alone as well as untreated plants, in which the transplant water contained no toxicants, to serve as controls. The soil in the field plots had a high content of the causative organism of Granville wilt i.e. *Pseudomonas solanacearum*. After a 119-day growing season, the plants were examined and the roots graded on (1) crop response which was a rating on the size and vigor of the plants on a scale of 1 to 10 (1=poor, 10=excellent) and (2) Granville wilt development on a scale of 0 to 100 (0=no damage, 100=maximum disease development) and crop yield. The results of this examination and grading are set forth below in Table XI.

TABLE XI

| Test Compound | Dosage rate in pounds of active agent per acre | Crop response | Granville Wilt development | Crop yield in pounds per acre |
|---|---|---|---|---|
| 6-chloro-2-methoxy-4-(trichloromethyl)pyridine plus O-ethyl S,S-dipropyl-phosphoro-dithioate | 0.5 6 | 8.3 | 26 | 2,296 |
| O-ethyl S,S-dipropyl-phosphoro-dithioate | 6 | 6.7 | 40 | 1,772 |
| Control | — | 5.7 | 62 | 1,636 |

Preparation of Active Compounds

2,6-Dichloro-4-(dichloromethyl)pyridine

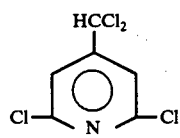

To a solution of 73 grams (0.275 mole) of 2,6-dichloro-4-(trichloromethyl)pyridine dissolved in 125 milliliters of acetone was added a solution of 108 grams (0.48 mole) of stannous chloride hydrate and 40 milliliters of concentrated hydrochloric acid in 500 milliliters of acetone. The mixture was refluxed for 2.0 hours. The solid which formed was separated by filtration and three fourths of the solvent was thereafter removed by evaporation. The remainder of the reaction mixture was diluted with water and the oil phase which formed, removed by extraction with hexane. The 2,6-dichloro-4-(dichloromethyl)pyridine product was dried and recovered from the solvent by evaporation of the solvent. The product had a boiling point of 123°- 126° C. at 1.6 millimeters of mercury.

2,6-Dichloro-4-(dichlorofluoromethyl)pyridine

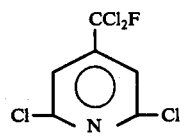

A mixture containing 138.5 grams (0.522 mole) of 2,6-dichloro-4-(trichloromethyl)pyridine and 34 grams (0.187 mole) of Antimony trifluoride was heated to 80°-84° C. and maintained under agitation for 23 minutes. During this step, a slow stream of chlorine gas was passed over the surface of the reaction mixture. The reaction mixture was steam distilled and the crude 2,6-dichloro-4-(dichlorofluoromethyl)pyridine product was purified by fractionation. The product had a boiling point of 74°-76° C. at 1.0 millimeter of mercury.

The 2,6-dibromo- counterparts of the above 2,6-dichloro compounds can be prepared by conventional halogen exchange. They can also be prepared by employing 2,6-dibromo-4-(trichloromethyl)pyridine as the starting material in the above procedure.

The compounds employed in the present method which corresponds to the formula

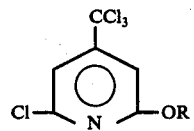

wherein R is lower alkyl of 1 to 4 carbon atoms or phenyl are all known and are taught in U.S. Pat. No. 3,244,722. These compounds are prepared by reacting 2,6-dichloro-4-(trichloromethyl)pyridine with the sodium salt of the appropriate hydroxy compound in a solvent at a temperature of from about 60° to about 120° C. for about 0.5 to 10 hours.

The compound employed in the present method which corresponds to the formula

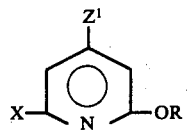

wherein $Z^1$ represents dichloromethyl or dichlorofluoromethyl and X and R as hereinbefore defined can be prepared by the following general procedure as outlined above in U.S. Pat. No. 3,244,722 employing the appropriate halogenated dichloromethyl or dichlorofluoro pyridine and alcohol starting materials.

What is claimed is:

1. A method for protecting plants planted in soil containing soil-borne plant disease organisms of the genera Verticillium, Rhizoctonia, Phytophthora, Pythium and Pseudomonas for an extended time period, of a minimum of 3 weeks, from attack by said soil-borne plant disease organisms which comprises contacting plant parts with a non-phytotoxic plant protecting amount of a systemic plant protectant corresponding to the formula

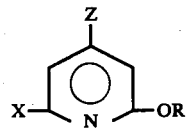

wherein X represents chloro, fluoro or bromo; Z represents trichloromethyl, dichloromethyl or dichlorofluoromethyl and R represents lower alkyl of 1 to 4 carbon atoms or phenyl, in intimate admixture with an inert adjuvant therefor.

2. The method as defined in claim 1, wherein the plant parts are contacted with the plant protector prior to being attacked by plant disease organisms.

3. The method as defined in claim 1 wherein the plant parts are contacted with the plant protector after being attacked by plant disease organisms.

4. The method as defined in claim 1 wherein the below ground plant parts are contacted with the systemic plant protectant.

5. The method as defined in claim 1 wherein the above ground plant parts are contacted with the systemic plant protectant.

6. The method as defined in claim 1 wherein plant seeds are contacted with the systemic plant protectant.

7. The method as defined in claim 1 wherein plant storage organs are contacted with the systemic plant protectant.

8. The method as defined in claim 1 wherein the systemic plant protectant is 6-chloro-2-methoxy-4-(trichloromethyl)pyridine.

9. The method as defined in claim 1 wherein the systemic plant protectant is 6-bromo-2-methoxy-4-(trichloromethyl)pyridine.

10. The method as defined in claim 1 wherein the systemic plant protectant is 6-chloro-2-methoxy-4-(dichloromethyl)pyridine.

11. The method as defined in claim 1 wherein the systemic plant protectant is 6-chloro-2-methoxy-4-(dichlorofluoromethyl)pyridine.

12. The method as defined in claim 1 wherein the systemic plant protectant is 6-fluoro-2-methoxy-4-(trichloromethyl)pyridine.

13. The method as defined in claim 1 wherein the systemic plant protectant is 6-chloro-2-ethoxy-4-(trichloromethyl)pyridine.

14. The method as defined in claim 1 wherein the systemic plant protectant is 6-chloro-2-n-butoxy-4-(trichloromethyl)pyridine.

15. The method as defined in claim 1 wherein the systemic plant protectant is 6-chloro-2-phenoxy-4-(trichloromethyl)pyridine.

* * * * *